United States Patent [19]

Yonetani et al.

[11] Patent Number: 6,087,087
[45] Date of Patent: Jul. 11, 2000

[54] TREATMENT OF HEMOGLOBIN WITH NITRIC OXIDE

[75] Inventors: Takashi Yonetani, 2400 Chestnut St., Apt. 2507, Philadelphia, Pa. 19103-4324; Antonio Tsuneshige, Philadelphia, Pa.

[73] Assignees: Takashi Yonetani, Philadelphia, Pa.; Foryou Corporation, Tokyo, Japan

[21] Appl. No.: 09/109,267

[22] Filed: Jul. 2, 1998

Related U.S. Application Data

[60] Provisional application No. 60/051,680, Jul. 3, 1997.

[51] Int. Cl.[7] ............................... A01N 1/02; B24C 5/08
[52] U.S. Cl. ............................................. 435/2; 424/93.73
[58] Field of Search ............................... 424/93.73; 435/2

[56] References Cited

U.S. PATENT DOCUMENTS 5,834,030  11/1998  Bolton .................................... 424/613

FOREIGN PATENT DOCUMENTS

WO 97/10265   3/1997   WIPO .

OTHER PUBLICATIONS

Cassoly, R., "Use of Nitric Oxide As a Probe for Assessing the Formation of Asymmetrical Hemoglobin Hybrids," *J. Biol. Chem.* 253:3602–3606 (1978).
Doyle, M.P., and Hoekstra, J.W., "Oxidation of Nitrogen Oxides by Bound Dioxygen in Hemoproteins," *J. Inorg. Chem.* 14:351–358 (Jul. 1981).
Fujii, M., et al., "The Porphyrin–Iron Hybrid Hemoglobins. Absence of the Fe–His bonds in one type of subunits favors a deoxy–like structure with low oxygen affinity," *J. Biol. Chem.* 268:15386–15393 (Jul. 1993).
Henry, Y., and Banerjee, R., "Electron Paramagnetic Studies of Nitric Oxide Haemoglobin Derivatives: Isolated Subunits and Nitric Oxide Hybrids," *J. Mol. Biol.* 73:469–482 (Feb. 1973).
Hille, R., et al., "Spectral transitions of nitrosyl hemes during ligand binding to hemoglobin," *J. Biol. Chem.* 254:12110–12120 (Dec. 1979).
Kosaka, H., et al., "ESR spectral transition by arteriovenous cycle in nitric oxide hemoglobin of cytokine–treated rats," *Am. J. Physiol.* 266:C14000–C1405 (May 1994).
Kosaka, H., and Seiyama, A., "Physiological Role of Nitric Oxide as an Enhancer of Oxygen Transfer from Erythrocytes to Tissues," *Biochem. Biophys. Res. Commun.* 218:749–752 (Jan. 1996).
Kosaka, H., and Seiyama, A., "Elevation of oxygen release by nitroglycerin without an increase in blood flow in the hepatic microcirculation," *Nature Medicine* 3:456–459 (Apr. 1997).
Nagai, K., et al., "The Effect of Quaternary Structure on the State of the α and β Subunits within Nitrosyl Haemoglobin. Low temperature photodissociation and the ESR spectra," *Biochem. Biophys. Acta* 532:17–28 (Jan. 1978).

Moore, E.G., and Gibson, Q.H., "Cooperativity in the dissociation of nitric oxide from hemoglobin," *J. Biol. Chem.* 251:2788–2794 (May 1976).
Pepke–Zaba, J., et al., "Inhaled nitric oxide as a cause of selective pulmonary vasodilatation in pulmonary hypertension," *Lancet* 338:1173–1174 (Nov. 1991).
Taketa, F., et al., "Chain Nonequivalence in Binding of Nitric Oxide to Hemoglobin," *J. Biol. Chem.* 253:5448–2451 (1978).
Traylor, T.G., and Sharma, V.S., "Why NO?," *Biochemistry* 31:2847–2849 (Mar. 1992).
Tsuneshige, A., and Yonetani, T., "Functional Studies of the Interaction of Hemoglobin (HbA) with NO And $O_s$. Binding of Nitric Oxide to α–Subunits of HbA Converts HbA to a Low–Affinity, Allosteric $O_2$–Carrier thus NO is a Negative Allosteric Effector of HbA to Facilitate Effective Oyxgen Delivery," *Biophys. J.* 70:A220 (1996).
Yonetani, T., et al., "Electromagnetic Properties of Hemoproteins. V. Optical and Electron Paramagnetic Resonance Characteristics of Nitric Oxide Derivatives of Metalloporphyrin–Apohemoprotein Complexes," *J. Biol. Chem.* 247:2447–2455 (Apr. 1972).
Yonetani, T., "Nitrogen Monoxide (NO) in the Blood. Poison Gas or Life Saver? EPR, NMR, and Functional Studies of the Interaction of Hemoglobin (Hb) with NO," *Proc. Japanese Medical Soc. Magn. Resom,* Kanagawa, Japan (1995).
Yonetani, T., and Tsuneshige, A., "Nitric Oxide (NO) in the Blood: EPR, NMR, and Functional Studies of the Interaction of Hemoglobin (HbA) with NO, show that NO is a Negative Allosteric Effector of HbA to Facilitate Effective Oxygen Delivery," *Biophys. J.* 70:A220 (1996).
Yonetani, T., "Nitric Oxide in the Blood: Coordination chemistry, magnetic resonance, and biological function," *Proc. 35th ESR Discussion Conference,* Yamagata, Japan, p. 15, Abstract No. 106S (1996).
Imai, *Allosteric effects in haemoglobin,* Cambridge University Press, London (1982).
Chen et al., *Biophysical Journal,* 74:A80 (1998).
Gibson et al., *Proc. Roy. Soc. London B. Biol. Sci.* 163:197–205 (1965).
Jia et al., *Nature* 380:221–226 (1996).
Huang, *J. Biol. Chem.* 254:22:11467–11474 (1979).
Imai et al., *Biochemica et Biophysica Acta* 490:164–170 (1977).
Shiga et al., *Biochemistry* 8:1:378–383 (1969).
Perutz, *Nature* 228:726–739 (1970).
Rein et al., *Febs Letters* 24:1:24–26 (1972).

(List continued on next page.)

*Primary Examiner*—Sandra E. Saucier
*Attorney, Agent, or Firm*—Birch, Stewart, Kolasch & Birch, LLP

[57] ABSTRACT

Methods and compositions are provided for treating diluents (including whole blood or at least one blood component) comprising hemoglobin containing erythrocytes (i.e., red blood cells), in order to increase the oxygen delivery capacity of the hemoglobin, wherein nitric oxide is bound to most or all of the hemoglobin present in said erythrocytes as α-nitrosyl-hemoglobin or its oxygen bound forms.

16 Claims, 6 Drawing Sheets

OTHER PUBLICATIONS

Wayland et al., *J Amer. Chem. Soc.* 96:19:6037–6040 (1974).

Maxwell et al., *Biochemistry* 15:2:388–396 (1976).

Nagai et al., *Proc. Natl. Acad. Sci. USA* 77:4:2033–2037 (1980).

Suzuki et al., *Biochem. and Biophy. Res. Commun.* 19:6:691–695 (1965).

Beckman et al., *Proc. Natl. Acad. Sci. USA,* 87:1620–1624 (1990).

Ignarro et al., *Proc. Natl. Acad. Sci. USA,* 84:9265–9269 (1987).

Hayashi et al., *J. Biol. Chem.* 241:1:79–884 (1966).

Yonetani et al., *J. Biol. Chem.* 273:32:20323–20333 (1998).

Eriksson et al., "Binding of Nitric Oxide to Intact Human Erythrocytes as Monitored by Electron Paramagnetic Resonance", BBRC 203 : 176–1811 (1994).

Minamiyama et al., "Effect of Thiol Status on Nitric Oxide Metabolism in the Circulation", Arch. Biochem. Biophys. 3411 : 186–192 (1997).

FIG.1A
Hb
FIG.1B
α(porphyrin)$_2$β(Fe)$_2$
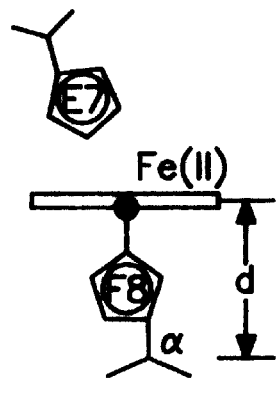
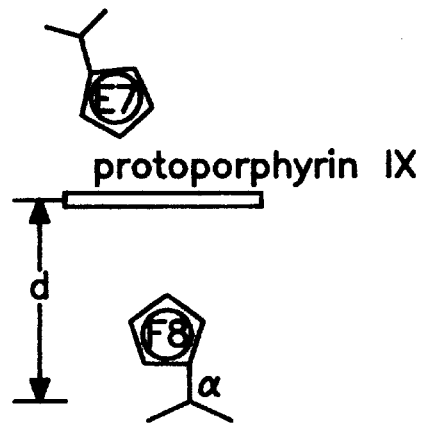
FIG.1C
HbM$_{Iwate}$
Distal Side
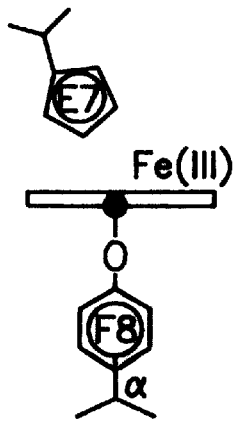
Proximal Side
FIG.1D
HbM$_{Boston}$
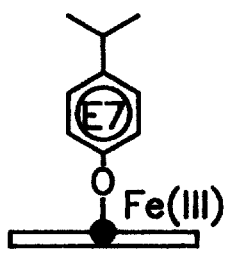
FIG.1E
Hb(NO)$_4$+IHP
or
α(Fe-NO)$_2$β(Fe)$_2$
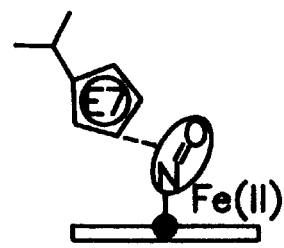

6,087,087

TREATMENT OF HEMOGLOBIN WITH NITRIC OXIDE

This application claims the benefit of the filing date of provisional application 60/051,680 filed on Jul. 3, 1997, which is herein incorporated by reference.

BACKGROUND OF THE INVENTION

1. Field of the Invention

The present invention relates to the use of nitric oxide to treat hemoglobin-containing erythrocytes in a diluent, including whole blood or at least one blood component, as well as compositions and methods of making and using thereof.

2. Related Background Art

Similarities Between Carbon Monoxide and Nitric Oxide

Carbon monoxide, a well-known environmental pollutant, has a high affinity for hemoglobin (Hb) and causes CO poisoning by binding to the heme groups of Hb in competition with $O_2$. Its binding not only reduces the $O_2$ binding capacity of Hb but also modifies Hb toward a high-affinity state rendering Hb incapable of delivering $O_2$ to peripheral tissues effectively. Furthermore, the so-formed CO-bound Hb is highly stable and its toxic effect on the mammalian physiology is persistent and cumulative. The U.S. Environmental Protection Agency specifies the occupational limits of CO to be 8 ppm for 9-hour, and 35 ppm for 1-hour, inhalation for the adult, respectively (The U.S. Environmental Protection Agency, Publication AP-84 (1971)). Additionally, nitric oxide (also called nitrogen monoxide or NO) has more than a thousand-fold higher affinity for Hb than CO (Gibson, Q. H., and Roughton, F. J. W., Proc. Roy. Soc. London B. Biol. Sci. 163:197–205 (1965)). NO was thus expected to cause blood poisoning by reducing $O_2$ binding and delivery capacities as does CO, and thus be toxic if present in more than very low concentrations in the blood.

Physiological Effects of Nitric Oxide

While nitric oxide is produced in vivo by several different forms of NO synthases (NOS), it is present in very low concentrations in the blood (generally less than one micromolar). When present in the blood, as it is an uncharged diatomic molecule with limited stability, NO can readily penetrate through cellular structures and act as a paracrine on its primary target, soluble guanylyl cyclase, in local environments immediately after its production. Nitric oxide activates soluble guanylyl cyclase to produce cyclic guanosine monophosphate (cGMP) which, in turn, initiates cGMP-dependent cascade reactions, leading to a wide range of biochemical, cellular, and physiological responses.

Such responses result from a low steady-state concentration of NO ($<1 \mu M$) in the blood, which involve maintaining normal vascular tone and other necessary conditions for the systemic and pulmonary circulation. A delicate balance exists between production of NO by NOSs and sequestration of NO, primarily by Hb in the erythrocyte, that maintains the homeostasis of the NO concentration in the plasma. The concentration of NO in the plasma is sometimes altered during infection and inflammation and by administration of NOS inhibitors or NO-generating reagents, such as nitroglycerin and nitrite. Such changes can wreak havoc in the circulatory system. Constriction of blood vessels, resulting in elevated blood pressure, vascular adhesion of leukocytes, and aggregation of platelets have been observed when the concentration of NO is increased. Free NO in the plasma constantly diffuses into the erythrocyte and immediately reacts with Hb, which acts as a NO scavenger. Stoichiometric reactions of NO with oxyHb are apparently fast and have been used for a spectrophotometric assay of NO (Doyle, M. P., and Hoekstra, J. W., J. Inorg. Chem. 14:351–358 (1981)). Thus, it has been generally assumed that free NO in the blood is scavenged by rapid reaction with oxyHb to produce such bio-inactive products as metHb and nitrate under physiological conditions. The so-formed metHb is recycled back to bioactive deoxyHb by metHb reductase in the erythrocyte.

Kosaka and Seiyama reported that the $O_2$ binding curve of the blood of the rat treated with nitroglycerin was approximately 10 torr right-shifted (Kosaka, H. and Seiyama. A., Biochem. Biophys. Res. Commun. 218:749–752 (1996)) and observed increases in $O_2$ delivery in hepatic sinusoids in nitroglycerin-treated rats (Kosaka. H. and Seiyama, A., Nature Science 3:456–459 (1997)).

Addition of small quantities of nitric oxide (NO) to hemoglobin (Hb) in solution (Hille, R., et al., J. Biol. Chem. 254:12110–12120 (1979)) and in the erythrocyte (Kosaka, H., et al., Am. J. Physiol. 266:C1400–C1405 (1994)); Erikson, L. E. G., Biochem. Biophys. Res. Commun. 203:176–181 (1994) converts a small fraction of the total Hb molecules to α-nitrosylHb. Intravenous administration of nitroglycerin, nitrite, and some cytokines to rats partially converts Hb to α-nitrosylHb (Kosaka, H. and Seiyama. A., Biochem. Biophys. Res. Commun. 218:749–752 (1996); Kosaka. H. and Seiyama, A., Nature Science 3:456–459 (1997)). The maximal fraction of α-nitrosylHb produced in rats is, however, less than 2% of the total Hb in rats (Kosaka, H., et al., Am. J. Physiol. 266:C1400–C1405 (1994)); Erikson, L. E. G., Biochem. Biophys. Res. Commun. 203:176–181 (1994); Kosaka, H. and Seiyama. A., Biochem. Biophys. Res. Commun. 218:749–752 (1996); Kosaka. H. and Seiyama, A., Nature Science 3:456–459 (1997)).

Further addition of these NO-producing compounds results in increasing amounts of tetra-nitrosylHB and metHb, both of which have no ability to transport $O_2$ and thus are toxic (Kosaka, H., et al., Am. J. Physiol. 266:C1400–C1405 (1994)); Erikson, L. E. G., Biochem. Biophys. Res. Cornmun. 203:176–181 (1994); Kosaka, H. and Seiyama. A., Biochem. Biophys. Res. Commun. 218:749–752 (1996); Kosaka. H. and Seiyama, A., Nature Science 3:456–459 (1997)).

The only way to produce substantially pure α-nitrosylHb has been to physically separate Hb into α- and β-subunits, expose the isolated α-subunits to NO to produce α-nitrosyl subunits, and then recombine the isolated β-subunits to regenerate a tetrameric α-nitrosylHb, in which only α-subunits contain NO: $\alpha(Fe-NO)_2\beta(Fe)_2$. α-nitrosylHb was reported to be a low-affinity $O_2$ carrier. Yonetani, T., Proc. Japanese Medical Soc. Magn. Reson, (1995); Yonetani T., (Abstract 106S), Proc. 35th ESR Discussion Conference, Yamagata, Japan (1996), p. 15).

The Problem of Expired Blood in Blood Banks

Huge amounts of blood and blood products at blood banks are discarded after certain periods of storage (such as 2–3 weeks), due to expiration of the blood and blood products. This is because the concentration of both bisphosphoglycerate (BPG), a natural allosteric effecter, and the pH inside of the erythrocyte, decrease during storage and consequently the oxygen affinity of Hb increases due to conversion to the high affinity form, rendering the stored blood ineffective for transfusion due to low oxygen delivering capacity. As BPG is impermeable to the erythrocyte membrane, external administration of BPG to blood cannot restore its oxygen delivering capacity.

U.S. Pat. No. 5,122,539 (issued Jun. 16, 1992) describes a new allosteric effecter, which decreases oxygen affinity of hemoglobin. Its structure is unrelated to 2,3-BPG, the natural allosteric effecter of the erythrocyte, but its function is similar. However, due to its chemical structure, this compound is expected to not pass through the erythrocyte membrane, such that this method will not have any practical applicability for treating blood or blood products to increase oxygen delivery.

Accordingly, there is a long-felt need to provide methods and compositions that counteract the loss of BPG from stored blood or blood components, in order to increase its oxygen delivering capacity so that it can be used for longer periods of time and will not have to be discarded, usually at about three weeks after the storage is begun.

Citation of documents herein is not intended as an admission that any of the documents cited herein is pertinent prior art, or an admission that the cited documents are considered material to the patentability of any of the claims of the present application. All statements as to the date or representation of the contents of these documents is based on the information available to the applicant and does not constitute any admission as to the correctness of the dates or contents of these documents.

SUMMARY OF THE INVENTION

Accordingly, it is an object of the present invention to provide methods and compositions for treating blood or blood products so that they can be stored for longer periods of time before use in transfusions, or for treating expired blood to render it suitable for use by converting the high-affinity hemoglobin to a low affinity state. Such a conversion results in blood or blood products that are suitable for delivering $O_2$ to tissues in vivo. Such methods and compositions can be used for treating whole blood and blood components, including cellular blood components, in order to render them suitable for transfusion.

It is another object of the invention to provide a method whereby most or all of the Hb in an erythrocyte-containing diluent is converted to NO-bound Hb, as α-nitrosyl-Hb (or its oxygenated forms thereof), by treatment with nitric oxide or by treatment with compounds or gases that produce nitric oxide. The diluent can be any physiologically compatible solution, suspension or colloid (or mixture thereof), and can include whole blood or any blood components that also include erythrocytes (i.e., red blood cells or RBC's) from mammals, including humans. The method can also include treatment of blood or blood components to rejuvenate their oxygen delivery capability.

A further object of the present invention is to provide compositions containing treated RBCs having most or all of the Hb in the α-nitrosyl-Hb form (or its oxygenated forms), and a diluent. The diluent can be any solution, suspension or colloid (or combination thereof), and can include whole blood or any blood components that further include RBC's. The diluent is preferably physiologically compatible.

Other objects, features and advantages of the present invention will be set forth in the detailed description of preferred embodiments that follows, and in part will be apparent from the description or can be learned by practice of the invention. These objects and advantages of the invention will be realized and attained by the compositions and methods particularly pointed out in the written description and claims hereof.

In accordance with these and other objects, a first embodiment of the present invention is directed to a method for treating an erythrocyte containing diluent, comprising adding NO to the diluent to provide at least about 80 percent of the Hb in the erythrocytes as α-nitrosyl-Hb, or its oxygenated forms, and more preferably as at least about 80–99 percent, or any range or value therein, and preferably at least about 95–99 percent. In preferred embodiments of the present invention, the blood components are cellular blood components, such as red blood cells (RBCs) and platelets, liquid blood components, such as plasma, or mixtures of cellular and/or liquid blood components.

A further embodiment of the present invention is directed to compositions comprising a diluent and erythrocytes having Hb, where at least about 80–99 percent of the Hb is in the form of α-nitrosyl-hemoglobin, or its oxygenated forms. Such compositions include whole blood or blood components that have been stored and are then treated using methods of the present invention to provide such compositions, where the diluent is the treated whole blood or blood component, or is derived therefrom as a blood product, as known in the art.

It is to be understood that both the foregoing general description and the following detailed description are exemplary and explanatory only and are intended only to provide further explanation of the present invention.

BRIEF DESCRIPTION OF THE FIGURES

FIGS. 1A–E is a schematic representation of the heme coordination structures of the α-subunits in Hb (A), α(porphyrin)$_2$β(Fe)$_2$ hybrid (Fujii, M., et al., *J. Biol. Chem.* 268:15386–15393 (1993)); (B), HbM$_{Iwate}$ (Hayashi, A., et al., *J. Biol. Chem.* 241:79–84 (1966)); (C), HbM$_{Boston}$ (Suzuki, T., et al., *Biochem. Biophys. Res. Commun.* 19:691–695 (1965)) (D), and Hb(fe-NO)$_4$+IHP (Rein, H., et al., *FEBS Lett.* 93:24–26 (1972); Wayland, B. B., and Olson, L. W., *J. Am. Chem. Soc.* 96:6037–6041 (1974); Maxwell, J. C., and Caughey, W. S., *Biochemistry* 15:388–396 (1976)) (inositol hexaphosphate) or α(Fe—NO)$_2$β(Fe)$_2$ (Yonetani T., (Abstract 106S), *Proc. 35th ESR Discussion Conference*, Yamagata, Japan (1996) p.15) (E). The common structural denominator of Low-Affinity Extreme Hbs is the broken or stretched/tilted link (→d←) between the heme Fe and the α-carbon of the proximal (F8) residue. (Fujii, M., et al., *J. Biol. Chem.* 268:15386–15393 (1993).)

C.) of α(Fe—NO)$_2$β(Fe)$_2$ (B) as a function of O$_2$, IHP, and pH. Relative fractions of the 5-coordinate were estimated by EPR simulation as described in FIG. 1. Alpha-nitroylHb (0.5 mM heme) preparations were dissolved in 0.1 M bis-Tris buffer with 0.2 M Cl (pH 6.0–7.4), 0.1 M Tris buffer with 0.2 Cl (pH 8.0–9.0), and 0.1 M critic acid-phosphate buffer (pH 4.5–5.5). The pH dependency of the mid points of the coordination equilibrium (closed circle) between deoxyβ-subunits (——) and oxy β-subunits (===) in Panel A is in good agreement with the Bohr effect of the O$_2$ affinity (P$_{50}$) of α-nitrosylHb (open square) in Panel B, though the measurements were made at different temperatures. This suggests that changes in the coordination equilibrium during freezing are slow and negligible. The Bohr effect of the O$_2$ affinity of Hb (open circle) is less sensitive to pH than that of α-nitrosylHb around pH 7.4 (ΔH$^+$≈−0.5 versus −0.9, respectively).

FIGS. 5A–D shows Hill plots of O$_2$ binding equilibria of Hb (open circle) and α-nitrosylHb (closed circle) in solution at pH 5.8 (A), 6.6 (B), 7.4 (C), and 8.2 (D). Oxygen equilibrium curves were recorded at 15° C. continuously by monitoring absorbance changes at 560 nm. It was determined that the alteration of α-nitrosylHb during oxygenation measurements was negligible at or below 15° C.

Figure 6A:
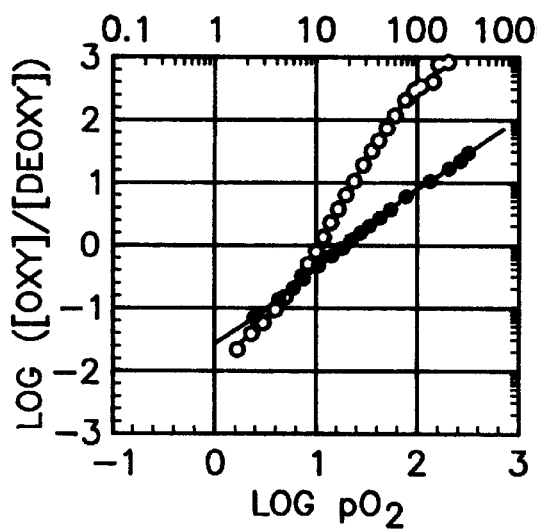
Figure 6B:
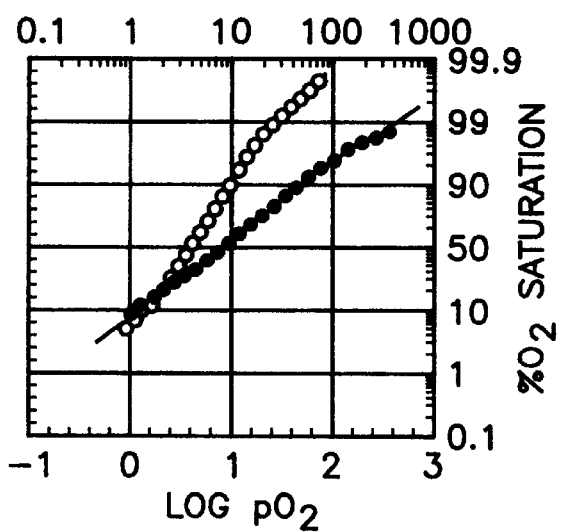

FIGS. 6A–B Hill plots of O$_2$ bindings equilibria of erythrocytes containing native Hb (open circle) and a α-nitrosylHb (closed circle) at pH 5.8 (A) and 7.4 (B). Oxygen equilibrium curves were measured using the Imai cell (Imai, K., *Allosteric Effects in Hemoglobin*, Cambridge University Press, London (1982)) in an Olis-Hitachi 557 dual-wavelength spectrophotometer (Bogart, Ga.). The dual-wavelength feature compensated the high light-scattering of the particulate suspensions. Changes in absorbance were monitored at 560 nm, with the reference beam fixed at 497 nm. The amount of Hb inside the erythrocyte was determined at 20 mM (heme) by measuring the Hb concentration in the supernatant after breaking a known amount of loosely packed erythrocytes in a hypotonic buffer and subjecting the cells to two cycles of freeze-thaw. Erythrocytes with and without the NO treatment were suspended in 50-fold volumes of 0.15 M phosphate buffer.

DETAILED DESCRIPTION

The present invention lies in the discovery by the present inventors that nitric oxide (NO) does not reduce the oxygen delivery capacity of hemoglobin (Hb), as previously thought, but instead increases this capacity, due to the formation of α-nitrosyl Hb, which was not previously thought to play any important role in the metabolism of NO in the circulatory system. The present inventors have discovered that Hb in erythrocytes can be treated to form α-nitrosyl Hb (or an oxygenated form thereof), which can carry oxygen in a mammalian circulatory system with enhanced efficiency.

The present invention provides methods and compositions involving the treatment of hemoglobin (Hb) containing erythrocytes in a diluent (as any solution, suspension or colloid or any combination thereof), where most or all of the hemoglobin has been converted to α-nitrosyl Hb, or an oxygenated form thereof, such as α-nitrosyl, β-oxy Hb. The present inventors have now discovered that such methods and compositions are suitable for treating blood and blood components to make them suitable for transfusion and thus extend the shelf life thereof, which presently become expired within about three weeks after they are removed from mammals, such as humans, and stored.

The present invention thus overcomes the long-standing problem of loss of bisphosphoglycerate (BPG) from stored blood and the resulting loss in oxygen delivery capacity of the blood and its unsuitability for use in transfusion. The methods and compositions of the present invention thus provide a means to rejuvenate expired, stored blood and blood components, at time periods including and beyond those presently available, such as 2–4 weeks.

The present invention is thus also useful for increasing the oxygen delivery capacity of Hb in erythrocytes, by forming α-nitrosyl Hb, or its oxygenated forms, while the Hb remains intact in the erythrocytes.

The present invention also provides methods and compositions for making and using such treated erythrocytes and diluents or blood components comprising such treated erythrocytes.

Definitions

Unless defined otherwise, all technical and scientific terms used herein are intended to have the same meaning as is commonly understood by one of ordinary skill in the relevant art. All patents and publications mentioned herein are expressly and entirely incorporated by reference.

As used herein, the term "blood components" is intended to mean one or more of the components that can be separated from whole blood and include, but are not limited to, cellular blood components, such as red blood cells and platelets; blood proteins, such as blood clotting factors, enzymes, albumin, plasminogen, and immunoglobulins; and liquid blood components, such as plasma and plasma-containing composition.

As used herein, the term "cellular blood component" is intended to mean one or more of the components of whole blood that comprises cells, such as red blood cells or platelets.

As used herein, the term "liquid blood component" is intended to mean one or more of the fluid, non-cellular components of whole blood, such as plasma (the fluid, non-cellular portion of the blood of humans or animals as found prior to coagulation) or serum (the fluid, non-cellular portions of the blood of humans or animals after coagulation).

As used herein, the term "composition or diluent containing blood or a blood component" is intended to mean a composition or diluent that contains a physiologically compatible solution, and one or more blood components. Such compositions can also contain a liquid blood component, such as plasma.

As used herein, a "transfusible diluent or composition" is intended to mean a diluent or composition that can be transfused into the circulatory system of a mammal, such as human. Transfusible compositions can contain whole blood, one or more blood components, such as one or more cellular blood components, one or more blood proteins, and one or more liquid blood components, or mixtures of whole blood and one or more blood components, such as clotting factors or plasma. Such a diluent or composition of the present invention preferably comprises NO-treated erythrocytes of the present invention.

As used herein, the term "extracellular pH" is intended to mean the pH of the liquid medium in which cellular blood components, such as red blood cells, are stored or maintained.

As used herein, the term "a physiologically acceptable solution" is intended to mean an aqueous solution which cellular blood components can be exposed, such as by being suspended therein, and remain viable, i.e., retain their essential biological and physiological characteristics. Such physiologically compatible solutions can preferably contain an effective amount of at least one anticoagulant. The term "a physiologically acceptable or compatible solution" is also intended to mean a physiologically compatible solution having a pH and osmotic properties (e.g, tonicity, osmolality and/or oncotic pressure) suitable for maintaining the integrity of the cell membrane of cellular blood components. Suitable physiologically acceptable or compatible buffered solutions typically have a pH between 5 and 8.5 and are isotonic or only moderately hypotonic or hypertonic. Physiologically compatible buffered solutions are known and readily available to those of skill in the art. Illustrative examples of suitable solutions include, but are not limited to, those listed in Table I below.

TABLE I

Common Physiologically compatible Buffered Solutions

| Ingredient | CPDA-1* (mM) | Unisol (mM) | Arc 8 (mM) |
| --- | --- | --- | --- |
| sodium citrate | 89.6 | 17.3 | 33.3 |
| citric acid | 15.6 | 2.7 | — |
| glucose | — | — | 139 |
| dextrose | 161.0 | 35.5 | — |
| $NaH_2PO_4$ | 16.1 | — | 2.9 |
| $Na_2HPO_4$ | — | 3.0 | 12.0 |
| Adenine | 2.0 | 2.2 | 2.0 |
| Mannitol | — | — | — |
| NaCl | — | 110.4 | — |
| KCl | — | 5.1 | — |
| $CaCl_2$ | — | 1.7 | — |
| $MgCl_2$ | — | 4.0 | — |
| $NaHCO_3$ | — | 40.0 | — |
| pH | 5.7 | 7.4 | 7.4 |

*CPDA-1 is sold by Baxter Travenol.

Basis of the Present Invention

Without being limited to any particular theory or mechanism, the present inventors have discovered that the widely assumed primary pathway of NO scavenging by Hb (Doyle, M. P., and Hoekstra, J. W., *J. Inorg. Chem.* 14:351–358 (1981)) is not the principal pathway of NO removal in the blood, where the plasma concentration of NO (<1 $\mu$M) is substantially lower than the concentration of oxyHb. Instead, free NO in the plasma binds to deoxyHb in the erythrocyte to form partially nitrosylated Hb. As the $O_2$-saturation of Hb as low as ~58% in pre-capillary blood vessels has been known, the normally estimated intra-erythrocyte concentrations of deoxyHb of ~0.2 to ~0.4 mM and 5 mlM heme in arterial and venous bloods, respectively, are possible lower limits.

Even then, these concentrations of deoxyHb are significantly higher (>100-fold or more) than the steady-state concentration of plasma NO. The high affinity of NO for deoxyHb ($K_D=5\times10^{-12}$ M and ~$10^{-15}$ M for 6- and 5-coordinate nitrosylHb, respectively) (Gibson, Q. H., and Roughton, F. J. W., *Proc. Roy. Soc. London B. Biol. Sci.* 163:197–205 (1965)) far exceeds the corresponding value expected for the reaction of NO with oxyHb. Thus, NO reacts with available deoxyHb rather than oxyHb in the erythrocyte under normal physiological conditions.

In fact, when small amounts of NO (at molar ratios of NO/Mb heme of ⅟₆₀ or less at 15° C.) are added to Hb in solution or in the erythrocyte, no immediate formation of metHb is detected (Yonetani, T., and Tsuneshige, A., *Biophys. J.* 70:A220 (1996)), in contrast to the currently held concept. (Doyle, M. P., and Hoekstra, J. W., *J. Inorg. Chem.* 14:351–358 (1981)). Instead, formation of nitrosylHb has been detected by electron paramagnetic resonance (EPR) spectroscopy (Yonetani, T., and Tsuneshige, A., *Biophys. J.* 70:A220 (1996); Kosaka, H., et al., *Am. J. Physiol.* 266:C1400–C1405 (1994); Erikson, L. E. G., *Biochem. Biophys. Res. Commun.* 203:176–181 (1994)). Hemoglobin, which consists of two pairs of $\alpha$- and $\beta$-subunits, each one carrying one $O_2$-binding ferrous heme group.

Since a nitrosylferrous heme complex contains one unpaired electron, Hb fully exhibits a characteristic EPR spectrum of a free radical type around the g≈2.0 region, that is an arithmetic sum of those derived from nitrosylhemes of $\alpha$- and $\beta$-subunits (Shiga, T., et al., *Biochemistry* 8:378–383 (1969)). Such an EPR spectrum contains a wealth of structural information like spin state, spin density distribution, and coordination structure of the nitrosylheme (Yonetani, T., et al., *J. Biol. Chem.* 247:2447–2455 (1972)). Upon addition of inositol hexaphosphate (IHP), a strong allosteric effecter that shifts Hb toward a low-affinity state, its EPR spectrum exhibits an additional spectral feature (Rein, H., et al., *FEBS Lett* 93:24–26 (1972)), which is characterized by a set of sharp triplet hyperfine signals. The origin of these triplet signals has been identified to the 5-coordinate structure of the nitrosylhemes in the $\alpha$-subunits (Wayland, B. B., and Olson, L. W., *J. Am. Chem. Soc.* 96:6037–6041 (1974); Maxwell, J. C., and Caughey, W. S., Biochemistry 15:388–396 (1976); Szabo, A., and Perutz, M. F., *Biochemistry* 15:4427–4428 (1976)), that is derived from the trans-axial breakage of the $\alpha$-heme Fe-proximal His(F8) bonds, caused by the NO ligation.

This is due to a coordination property of NO that is unique among diatomic ligands. The coordination of NO to ferrous heme weakens the affinity for the trans-axial ligand (Traylor, T. G., and Sharma, V. S., *Biochemistry* 31:2847–2849 (1992)). In other words, nitrosylheme is more stable as a 5-coordinate rather than a 6-coordinate. On the other hand, other diatomic ligands like CO and $O_2$ favor the 6-coordinate structure over the 5-coordinate, so that coordination of CO or $O_2$ strengthens the affinity for the trans-axial ligand. Whether or not the NO ligation causes the trans-axial bond breakage depends on the strength of the heme Fe-His bond.

The heme coordination structure in the $\alpha$-subunits of deoxyHb is more constrained than that in the $\beta$-subunits (Perutz, M. F., *Nature* 228:726–739 (1970)) and the heme Fe-His bonds in the $\alpha$-subunits of deoxyHb are weaker than that in the $\beta$-subunits (Nagai, K., and Kitagawa, T., *Proc. Natl. Acad Sci. USA* 77:2033–2037 (1980)). Thus, the ligation of NO to the $\beta$-subunits causes no breakage of the Fe-His bonds in the $\beta$-subunits. The NO-induced bond cleavage occurs exclusively in the $\alpha$-subunits in the physiological milieu. The appearance of the sharp triplet EPR signals in the absence of IHP is, thus, a clear qualitative indication of the ligation of NO to the $\alpha$-subunits.

Subunit structures and state of ligation of Hb are expressed by these conventions, where $\alpha$, $\beta$, (Fe), (porphyrin), (Fe—NO), and (FeO$_2$) represent $\alpha$-subunit, $\beta$-subunit, subunits containing deoxyheme, protoporphyrin IX, nitrosylheme, and oxyheme, as a prosthetic group, respectively. The subscripted number denotes the number of the subunits. The intra-erythrocyte concentration of $\alpha$-nitrosylHbs can sometimes reach as high as ~2% of the total heme of Hb or ~400 $\mu$M nitrosylheme, when the plasma concentration of NO is abnormally increased by various causes (Kosaka, H., et al., *Am. J. Physiol.* 266:C1400–C1405 (1994)).

Preferred Embodiments

Treating Erythrocytes in Whole Blood

As a first step when practicing methods or providing compositions of the invention using whole blood, whole blood is preferably drawn from a donor into a suitable physiologically compatible buffered solution containing an effective amount of at least one anticoagulant. Suitable anticoagulants are known to those skilled in the art, and include, but are not limited to, heparin, lithium, potassium or sodium oxalate (15 to 25 mg/10 mL blood), sodium citrate (40 to 60 mg/10 mL blood), heparin sodium (2 mg/10 mL blood), disodium EDTA (10 to 30 mg/10 mL whole blood) or ACD-Formula B solution (1.0 mL/10 mL blood).

The whole blood so collected can then be treated according to the methods of the present invention. Alternatively, the whole blood can first be separated into blood components, including, but not limited to, plasma, platelets and red blood cells, by any method known to those of skill in the art.

For example, blood can be centrifuged for a sufficient time and at a sufficient centrifugal force to sediment the red blood cells. Leukocytes collect primarily at the interface of the red cells and the plasma-containing supernatant in the buffy coat region. The supernatant, which contains plasma, platelets, and other blood components, can then be removed and centrifuged at a higher centrifugal force, whereby the platelets sediment.

Human blood normally contains about $7 \times 10^9$ leukocytes per liter. The concentration of leukocytes, which pellet with the red cells, can be decreased by filtering through a filter that decreases their concentration by selected orders of magnitude. Leukocytes can also be removed from each of the components by filtration through an appropriate filter that removes them from the solution.

In a preferred embodiment of this invention, the whole blood or blood component to be treated is obtained in, prepared in or introduced into gas permeable blood preservation bags, which are sealed and flattened to a width sufficiently narrow to permit light to irradiate the contents, such that any pathogenic contaminant present in the blood or blood component in the bag will be irradiated. Any such blood bag known to those of skill in the art can be used provided that the bag is transparent to the selected wavelength of light.

In a more preferred embodiment of this invention, the gas permeable blood preservation bag also contains oxygen.

The composition that is to be treated can also include any suitable physiologically compatible buffer known to those of skill in the art. Examples of such buffers include, but are not limited to, Unisol and ARC 8.

Following treatment in accordance with the method of this invention, the whole blood, blood components or composition containing one or more of these can be stored or transfused. Alternatively, after treatment of compositions such as red cell preparations or platelet-rich plasma, the composition can be centrifuged at a force sufficient to pellet the cellular components. The supernatant can be removed following centrifugation and the cells resuspended to reduce the concentration of residual products.

In a preferred embodiment, the following method provides treated erythrocytes having most or all of the Hb present as at least about 80–99 percent α-nitrosyl-Hb.

Erythrocytes as Starting Material

If using erythrocytes in solution, then erythrocytes in a suitable buffer solution can preferably be used with a slightly acidic buffer, such as pH 5–6.5, or any range or value therein.

Whole Blood as Starting Material

If whole blood is to be used, then, as a non-limiting example, anti-coagulated blood can be suspended in an excess volume of chilled buffer solution, which can contain a sugar. The solution is preferably isotonic. Non-limiting examples of sugar solutions include, glucose, sucrose, maltose and/or fructose, 25–500 mM, such as 25–100, 100–250, 250–500 mM, or any range or value therein. Any known and suitable salt buffers can be used. The solution can then be centrifuged at 500–3000 g for 3–90 minutes at 4–20 degrees C., or any range or value therein. The supernatant and/other layers (e.g., the buffy layer of leukocytes) can be removed and stored or discarded, and the precipitate of erythrocytes can be re-suspended in a fresh buffer solution, such as an isotonic sucrose solution. The centrifugal washing procedure can then be repeated 0–5 times.

The final concentration of hemoglobin in the washed erythrocytes is then determined using known methods, and can be preferably about 2–30 mM heme (or ca. 0.5–7.5 mM tetrameric hemoglobin), and preferably about 10–30 mM. The loosely packed precipitate of washed erythrocytes can then optionally be re-suspended in an excess volume (e.g., 1.5–10 times, preferably 1.5–4 times) of chilled buffer, pH 5–6.2, preferably 5.6–6.0, or any ranges or values therein).

Deoxygenation of Erythrocytes

The isolated erythrocytes (from blood, a blood component, or as isolated erythrocytes) can be preferably deoxygenated using any known and suitable methods. As a non-limiting example, argon or nitrogen gas can be used to displace and remove the oxygen from the Hb in the erythrocytes. Observing the change in the color of the erythrocyte suspension readily follows the progress of deoxygenation. After prolonged deoxygenation, the color changes from bright red (of oxy hemoglobin) to deep purple (of deoxy hemoglobin).

Nitric Oxide Treatment

To treated the resulting or stored erythrocytes, NO is contacted with the erythrocytes (preferably deoxygenated) to form mostly or all α-nitrosyl hemoglobin, using any suitable method, including contacting NO in the form of a gas, solid or liquid with the erythrocytes, such that at least about 80–99 percent of the Hb in the erythrocytes forms α-nitrosyl Hb, or its oxygenated forms, such as, but not limited to, α-nitrosyl, β-oxy Hb.

As a non-limiting example, a 2–20 fold excess (to heme) quantity of a solution of sodium dithionite ($Na_2S_2O_4$) or organic nitrosothiols such as nitrosoglutathione and S-nitrosocysteine can be added into the erythrocyte suspension and can then be mixed for 1–1000 minutes (or any range or value therein), and then can be preferably chilled (0–20 degrees C.). An excess (e.g. 51–80%, such as 52–55%) equivalent (to heme) quantity of a solution of sodium nitrite ($NaNO_2$) or organic nitrosothiols can then be introduced into the erythrocyte suspension. Sodium nitrite reacts stoichiometrically and immediately with sodium dithionite and forms nitric oxide that combines with the α-heme groups of hemoglobin to form α-nitrosyl Hb. A slightly acidic pH (pH 5.0–6.5, such as 5.8) can optionally be used to promote the formation of α-nitrosyl hemoglobin. Optionally, a ca. 1–10% (e.g., 2–5%) excess of nitrite or organic nitrosothiols can be added to ensure the ligation of NO to all the α-subunits of hemoglobin and thus reducing the possibility of unreacted hemoglobin molecules remaining. The addition of a large excess of sodium nitrite or organic nitrosothiols into the suspension is preferably avoided because the ligation of NO to the β-subunits can occur using larger quantities of nitrite.

The resulting suspension can then be stored for 5–500 minutes in cold (0–25 degrees C., such as 4 degrees C.) and then optionally washed with isotonic, deoxygenated isotonic sugar solution, e.g., to remove excess reagents and reaction byproducts.

If oxygenated α-nitrosyl Hb is to be used or is desired, then the treated erythrocyte suspension can be exposed to air or an oxygen-containing gas (or mixture thereof) to produce oxygenated α-nitrosyl hemoglobin (e.g., α-nitrosyl, β-oxy hemoglobin (α(Fe—NO)$_2$β((Fe—O$_2$)$_2$)). Electron paramagnetic resonance spectroscopy (EPR) can then optionally be used (e.g., as described in Example 1) to confirm the amount of formation of desired product. The resulting erythrocytes containing α-nitrosyl hemoglobin can be stored at 0–15 degrees C. for 1–120 days before use, e.g., to be added to other blood components for transfusion.

Alternatively, erythrocytes, as described herein, can be treated with NO gas, or with NO formed from alternative chemical reactions as known in the art, in order to provide treated erythrocytes according to the present invention. The NO provided by a chemical reaction can be added to the erythrocytes after, during or before the chemical reaction has taken place to produce the NO.

The following examples are illustrative only and are not intended to limit the scope of the invention as defined by the appended claims. It will be apparent to those skilled in the art that various modifications and variations can be made in the methods of the present invention without departing from the spirit and scope of the invention. Thus, it is intended that the present invention covers the modifications and variations of this invention provided they come within the scope of the appended claims and their equivalents.

EXAMPLE 1

When the heme Fe-His(F8) bonds and its α-subunits are weakened or broken by either mutation or chemical modification, Hb permanently locks itself into a new, extremely low-affinity functional state, termed the Low-Affinity Extreme state (Fujii, M., et al., *J. Biol. Chem.* 268:15386 (1993)). An artificially synthesized Hb hybrid, α(porphyrin)$_2$β(Fe)$_2$ (Fujii, M., et al., *J. Biol. Chem.* 268:15386 (1993)), and natural Hb mutants, HbM$_{Iwate}$ (α$_{58}$His→Tyr) (Hayashi, A., et al., *J. Biol. Chem.* 241:79–84 (1966)) and HbM$_{Boston}$(α$_{57}$His→Tyr) (Suzuki, T., et al., *Biochem. Biophys. Res. Commun.* 19:691–695 (1965)) represent such a state. The coordination structures of the prosthetic groups in their α-subunits are schematically compared in FIGS. 1B, C, and D, respectively. The common structural denominator of these Low-Affinity Extreme Hbs is neither the presence of the heme Fe, the nature of its valency state, nor the structure of the distal side. It is the loss or distortion/stretch of the link between heme Fe and the α-carbon of the proximal (F8) residue (←–d–→) in the α-subunits (Fujii, M., et al., *J. Biol. Chem.* 268:15386 (1993)). These Low-Affinity Extreme Hbs are functionally characterized as a non-cooperative, non-allosteric, extremely low-affinity state: oxygen-binding curves of these Hbs are hyperbolic (non-cooperative) with extremely low O$_2$-affinity and insensitivity to pH (no Bohr effect) and organic phosphates (non-allosteric).

Figure 2A:
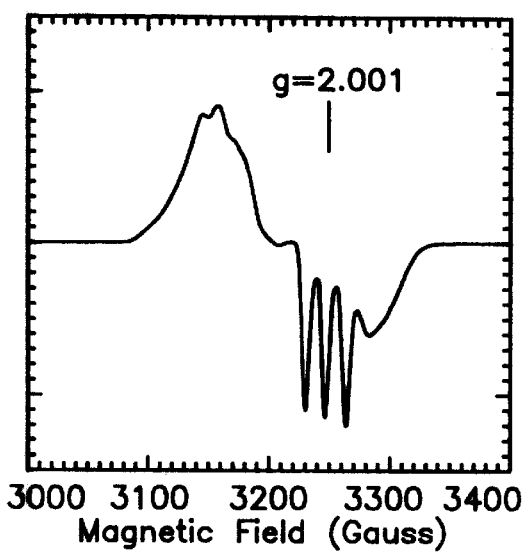
FIGS. 2A–D is an X-band EPR spectra of α-nitrosylHb [α(Fe—NO)$_2$β(Fe)$_2$] in the absence (A) and presence (B) of $O_2$. Hemoglobin preparations (0.5 mM heme) were dissolved in 0.1 M bis-Tris buffer, pH 7.4 containing 0.2 M Cl at 15° and frozen at liquid nitrogen temperature for EPR measurements. Changes between spectra A and B are reversible and depend on the $O_2$ binding to the β-subunits of Hb. Relative fractions of the 5-coordinate nitrosylhemes in the α-subunits of α-nitrosylHb were estimated to be ~80% and ~20% for spectra A and B, respectively, by EPR spectral simulation using the EPR spectrum of α-nitrosylHb with 2 nM IHP in the absence of $O_2$ at pH 4.8 (C) and that without IHP in the presence of $O_2$ at pH 9.0 (D) as standards for 100% and 0% 5-coordinates, respectively.
Figure 2C:
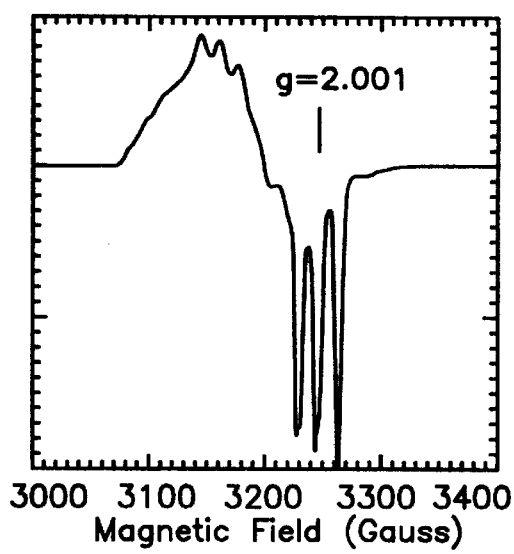
Figure 2B:
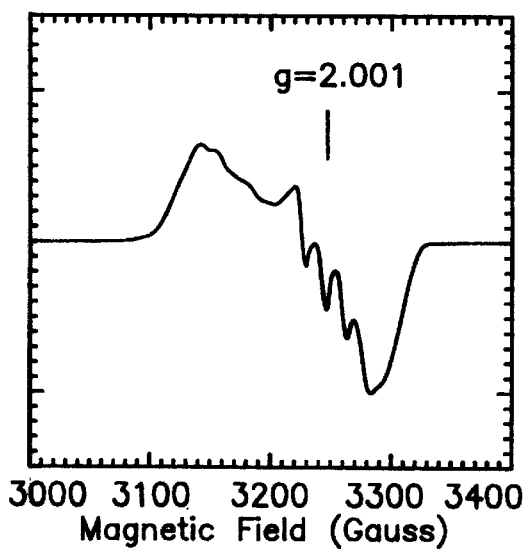
Figure 2D:
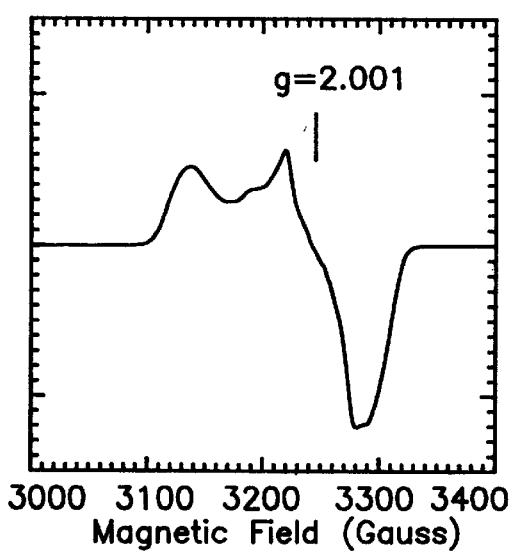
Figure 3:
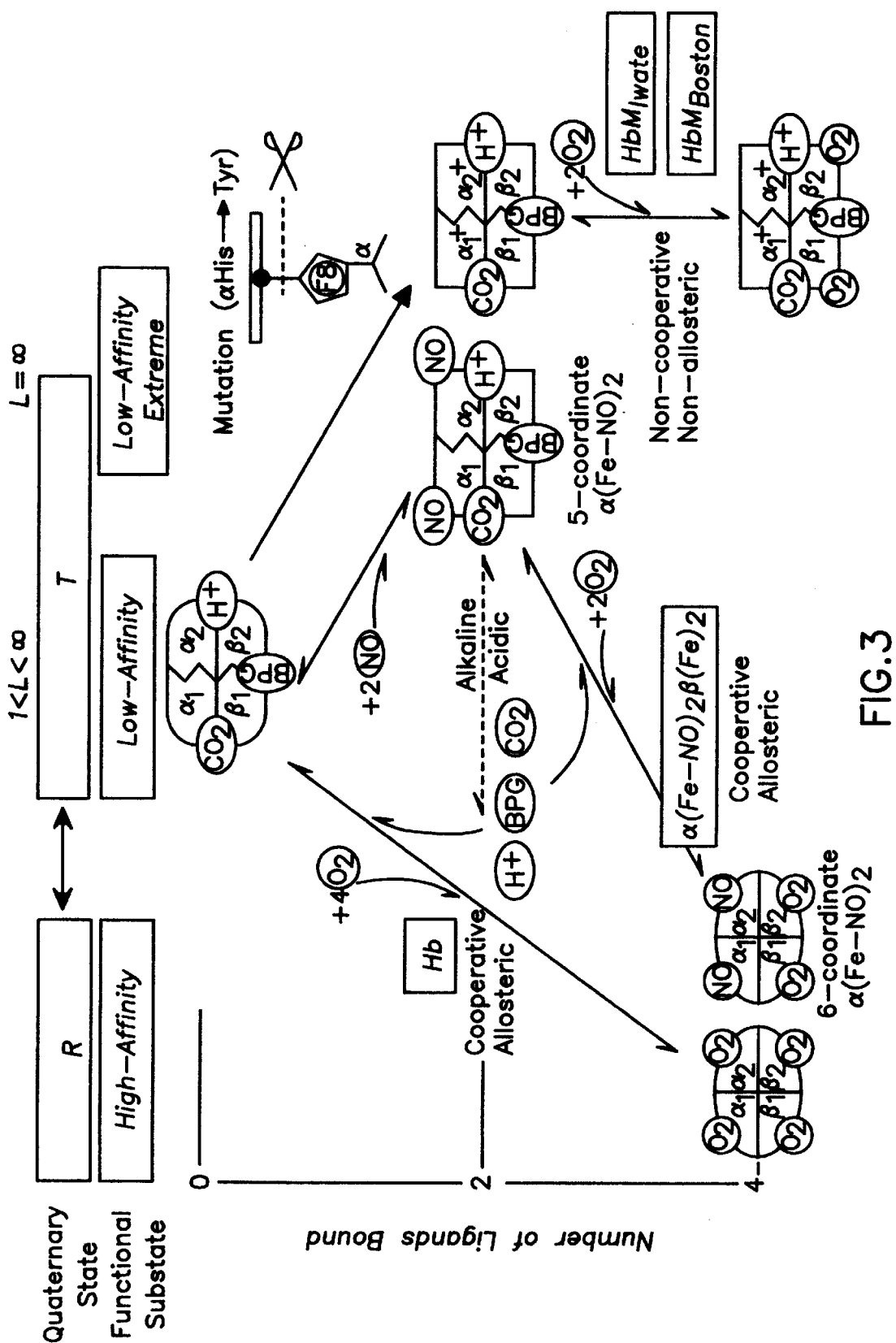
FIG. 3 is a schematic representation of the relationship between High-Affinity, Low-Affinity, and Low-Affinity Extreme states of Hb in the presence and absence of $O_2$ and allosteric effectors (H$^+$, BPG, and $CO_2$). Oxygenation takes place with Low-Affinity Extreme states, between Low-Affinity and High-Affinity states, and between low-Affinity Extreme and High-Affinity states for HbM, Hb, and α-nitrosylHb, respectively.
Figure 4A:
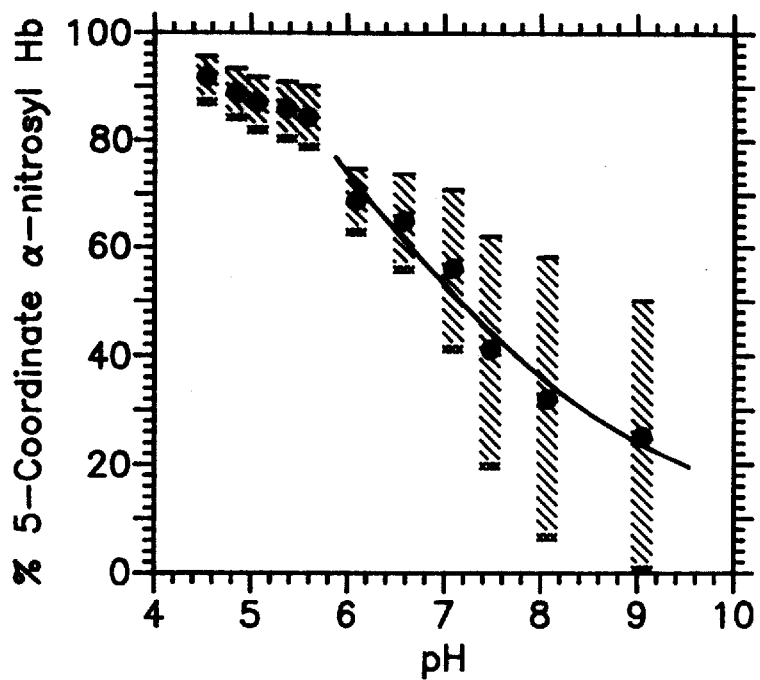
FIGS. 4A–B shows the Bohr effect (pH dependency) of the coordination equilibrium of the α-nitrosylheme species (A) and P$_{50}$ (partial pressure of $O_2$ at half saturation at 15°
Figure 4B:
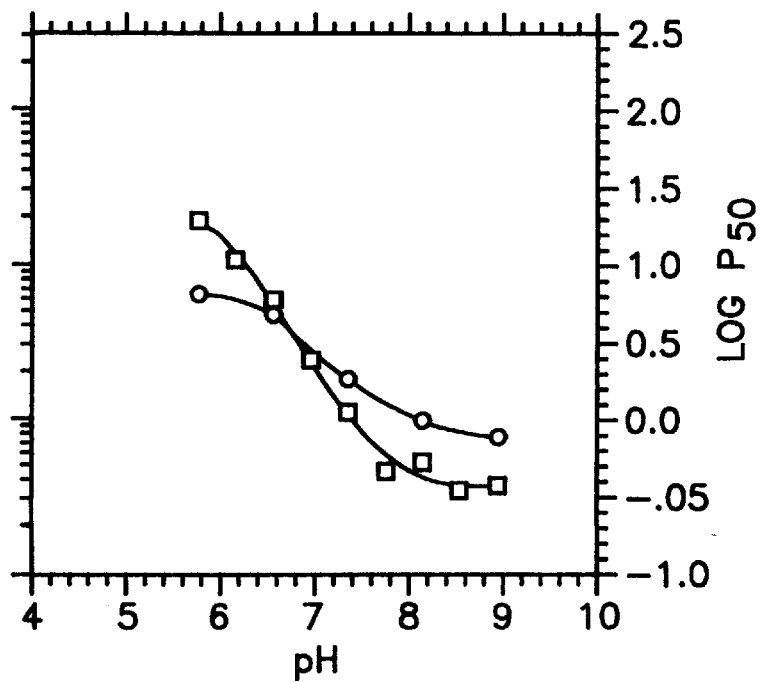

Purified α-nitrosylHb, α(Fe—NO)$_2$β(Fe)$_2$, show EPR spectra which change reversibly from predominantly 5- to predominantly 6-coordinate types upon reversible binding of O$_2$ to the β-subunits (FIGS. 2A and B). These results imply that α-nitrosylHB, α(Fe—NO)$_2$β(Fe)$_2$, is predominantly in a Low-Affinity Extreme state with broken α-nitrosylheme Fe-His (F8) bonds in the absence of O$_2$, whereas it becomes a High-Affinity state with the reformed α-nitrosylheme-His (F8) bonds in the presence of O$_2$, as is generally expected for a tetra-ligated, 6-coordinate Hb. Thus, the Low-Affinity Extreme state of α-nitrosylHb, α(Fe—NO)$_2$β(Fe)$_2$ changes reversibly to a High-Affinity state upon oxygenation, in contrast to HbM$_{Iwate}$ and HbM$_{Boston}$, whose Low-Affinity Extreme states are permanent and independent of oxygenation. The equilibrium between the 5- and 6-coordinate α-nitrosylheme species of α(Fe—NO)$_2$β(Fe)$_2$, is a complicated function of interactions with O$_2$, H$^+$, and organic phosphates like 2,3-bisphosphoglycerate (BPG) and IHP (FIG. 3). The 6-coordinate species (a High-Affinity state) are favored in the increased O$_2$ saturation at higher pH (FIG. 2D), whereas the 5-coordinate species (a Low-Affinity Extreme state) is dominant in the absence of O$_2$ and in the presence of IHP at lower pH (FIG. 2C). Oxygenation-induced shifts in the coordination equilibrium are larger at higher pH, whereas it becomes progressively smaller at lower pH (FIG. 4). At pH4.8 in the presence of IHP, the α-nitrosylhemes of α(Fe—NO)$_2$β(Fe)$_2$ become essentially a (~100%) 5-coordinate (FIG. 2C), and their coordination state becomes almost independent of O$_2$, indicating that α(Fe—NO)2β(Fe)$_2$ approaches a Low-Affinity Extreme state under such conditions. Thus, the O$_2$ binding of αFe—NO)2β(Fe)$_2$ is expected to become noncooperative and allosterically insensitive with extremely low affinity at acidic extreme.

Figure 5A:
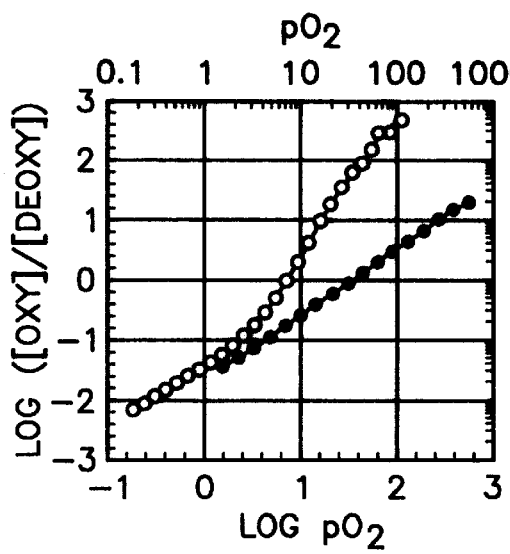
Figure 5B:
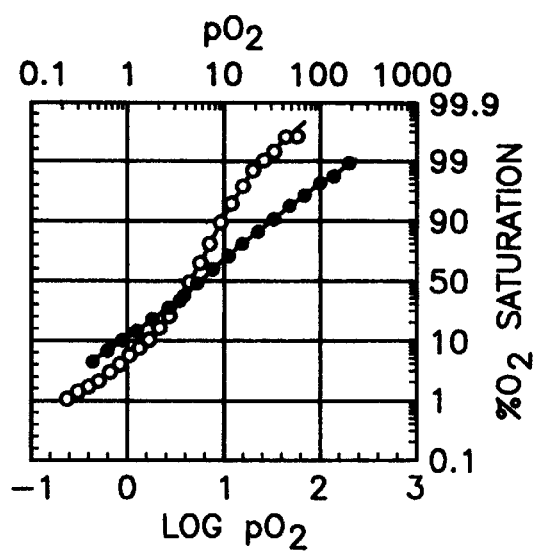
Figure 5C:
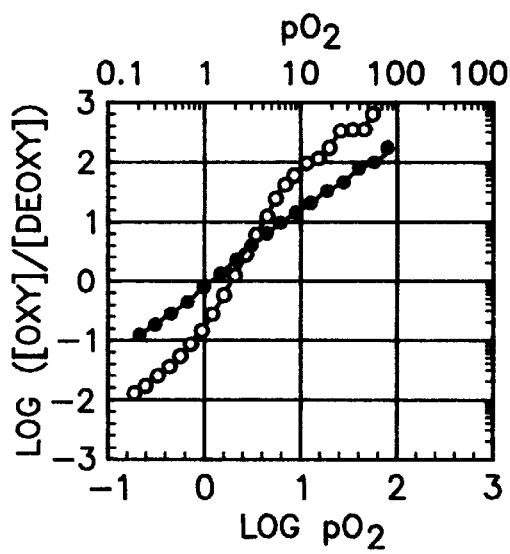
Figure 5D:
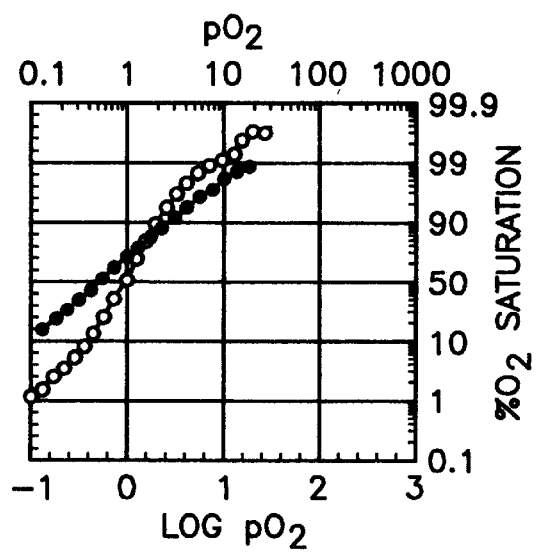

Alpha-nirosylHb, α(Fe—NO)$_2$β(Fe)$_2$, shows the O$_2$-binding behaviors (FIG. 5) predicted from the results of the EPR measurements of its coordination equilibrium mentioned above (FIG. 4). Alpha-nitrosylHb behaves as a cooperative, high-affinity O$_2$ carrier at alkaline pH, much like the partially CO-bound Hb (FIG. 5D). It becomes an essentially non-cooperative, low-affinity O$_2$ carrier at acidic pH (FIG. 5A), just like permanent Low-Affinity Extreme Hbs such as α(porphyrin)$_2$β(Fe)$_2$, HbM$_{Iwate}$ and HbM$_{Boston}$. In mid pH ranges, they become cooperative and allosterically sensitive O$_2$ carriers with varied O$_2$ affinity (FIGS. 5B and C). Thus, α-nitrosylHb, α(Fe—NO)$_2$β(Fe)$_2$, can be transformed to a series of High-Affinity, Low-Affinity, and Low-Affinity Extreme states of Hb by controlling the binding of O$_2$, H$^+$, BPG or IHP.

Carbon dioxide, another physiological allosteric effector that is abundant in the peripheral tissue, can probably influence α-nitrosylHb just like other effectors. Since its O$_2$ affinity continually decreases at lower pH (ΔH$^+$=−0.9 at and below pH 7.4), the Bohr effect of α-nitrosylHb is physiologically more favorable than Hb in terms of the efficiency in O$_2$ delivery to peripheral tissues. Thus, the allosteric effect of CO$_2$ on α-nitrosylHb becomes important in physiological milieu. On the other hand, the decrease of the O$_2$ affinity of Hb levels off around neutral pH (ΔH$^+$=−0.5 around pH 7.4), so that Hb is less effective in the delivery of O$_2$ to tissues at acidic pH values.

We have devised a method to convert essentially all the Hb molecules inside of the intact erythrocyte to α-nitrosylHb by slowly infusing NO into the erythrocyte and examined its O$_2$-binding characteristics in order to assess its possible role in a more physiological environment. (See, Example 4.) Contrary to expectation, α-nitrosylHb is found to be surprisingly stable against oxidation to metHb even under aerobic conditions. Prepared α-nitrosylHb, both in solution as well as within the erythrocytes, indicates no detectable formation of metHb during aerobic storage at 0° C. for an extended period of several days. Oxygen-binding characteristics of the intra-erythrocyte α-nitrosylHb (FIG. 6) essentially confirm those of the solution data (FIG. 5), except that effects of organic phosphate cannot be quantitatively estimated, as they are impermeable to the erythrocyte membrane. Furthermore, the intra-erythrocyte levels of BPG can vary according to the age and metabolic activity of the erythrocyte and the conditions of storage and experimental medium. Nevertheless, it is clear that α-nitrosylHb in the erythrocyte is unexpectedly capable of delivering $O_2$ to tissues more effectively than Hb, though it has only one-half of the $O_2$-carrying capacity of Hb.

OxyHb, α-nitrosylHb and tetra-nitrosylHb are eventually oxidized to metHb under aerobic conditions at higher temperatures, whereas the sequestered NO is never released from the α-hemes as free NO. Instead, it is oxidized to nitrate. Half-times of oxidation to metHb of 39, 29, and 27 hours at 15° C. decrease to 780, 120, and 38 minutes at 37° C. for oxyHb, α-nitrosylHb and tetra-nitrosylHb, respectively. The formed metHb is recycled to bioactive Hb by Hb reductase within the erythrocyte and nitrate is excreted to complete the NO scavenging.

Since the steady-state concentration of detectable α-nitrosylHb in the erythrocyte never exceeds ~2% (or ~400 μM) of the total heme of Hb in vivo, its overall effect on the $O_2$ binding characteristics of the blood can be apparently negligible. Recently, the nitroglycerin-induced increase in $O_2$ delivery in the hepatic sinusoid of rats has been attributed to the efficient delivery of $O_2$ by α-nitrosylHb (Kosaka, H., and Seiyama, A., *Nature Medicine* 3:456–459 (1997)). However, nitroglycerin-induced formation of α-nitrosylHb is only less than 2% of the total heme of Hb (Kosaka, H., et al., *Am. J. Physiol.* 266:C1400–C1405 (1994)). Therefore, the reported observation is, in fact, the definitive proof that some factors other than α-nitrosylHb are apparently responsible for the observed increase in the $O_2$ delivery to the tissue.

However, the NO locally generated near pre-capillary small vessels without vascular smooth muscles (which are known to contain eNOS) could transform substantial amounts of Hb to α-nitrosylHb, allowing more efficient local delivery of $O_2$ to peripheral tissues, especially under acidic conditions. The metabolically active brain, the organ that is most sensitive to hypoxic damage, has no obvious mechanism of protection against anoxia/hypoxia. However, it is known that high levels of NOSs exist in the brain. It can be that some of these NOSs can be involved in the activation of Hb to α-nitrosylHb for more effective delivery of $O_2$ to circumvent anoxia/hypoxia to the organ. The effect of the locally generated NO on the $O_2$ saturation of the intra-erythrocyte Hb in pre- and post-capillary small vessels must be measured to answer such a hypothesis.

We have shown that NO binds to Hb as a "negative allosteric" ligand during its initial binding to the α-subunits at acidic and neutral pHs and that $O_2$ acts as a homotropic (or "positive allosteric") ligand in the subsequent binding to the β-subunits. Since its bond-breaking ability is diminished at higher pH, NO binds to Hb solely as a homotropic ligand at alkaline pH, analogous to any other diatomic ligands (CO and $O_2$). Therefore, α-nitrosylHb behaves like a partially CO-bound Hb during oxygenation at alkaline pH (FIG. 4D). Once the dual nature of the Hb-NO interaction is understood, anomalous observations in kinetic and thermodynamic studies of reactions of deoxyHb and No, i.e., inconsistencies with the two-state allosteric model (Hille, R., et al., *J. Biol. Chem.* 254:12110–12120 (1979) Moore, E. G., and Gibson, Q. H., *J. Biol. Chem.* 251:2788–2794 (1976)), can be readily explained. The mutual dependence of the coordination structure and the ligand affinity between partner α-nitrosylHb is a testament to the delicate molecular structure of Hb that allows the transfer of structural information between one type of subunits and another.

Recently a new physiological role of Hb as a reversible NO carrier at the $β^{93}$Cys-SH sites through S-nitrosation has been proposed (Jia, L., et al., *Nature* 380:221–226 (1996)). However, both arterial and venous bloods contain sufficient amounts of deoxyHb. The affinity of deoxyHb at the heme groups for NO ($K_D$=5×10$^{-12}$M and ~10$^{-15}$M for 6- and 5-coordinates, respectively) (Gibson, Q. H., and Roughton, F. J. W., *Proc. Roy. Soc. London B. Biol. Sci.* 163:197–205 (1965)) is extraordinarily high in comparison to a presumed affinity of the $β^{93}$Cys-SH groups of oxyHb for NO. Since S-nitrosation between —SH and NO can be coupled with a one-equivalent redox reaction (—SH+NO⇌—S$^-$NO$^+$+H$^+$+e$^-$), a true affinity of the sulfhydryl group for NO cannot be well defined. Accordingly, whether or not such S-nitrosation reactions are expected to occur under physiological conditions and play a significant role in respiratory physiology must be more carefully examined.

We have shown that during the scavenging of NO through binding at the α-subunits, Hb transforms itself into α-nitrosylHb, a new $O_2$ carrier that is more efficient than normal Hb in $O_2$ delivery to peripheral tissues where pH is more acidic due to high metabolic activities. This feat is accomplished by utilizing the unique property of NO that can break the trans-axial Fe-ligand bond and by adapting a constrained heme coordination structure in its α-subunits that readily responds to NO by breaking the Fe-His bonds. This explains why NO causes no acute adverse effect on newborn infants during clinical treatments with inhaled NO, although NO has a substantially higher (>10$^3$) affinity for Hb than CO, the culprit of respiratory CO poisoning. Thus, Hb is found to be more agile than we have previously assumed. Hemoglobin can function simultaneously as a NO scavenger as well as an efficient $O_2$ carrier in the hostile environment of the blood, where NO, a high-affinity ligand, is always present.

Methods

Preparation of α-nitrosylHb, α(Fe—NO)$_2$β(Fe)$_2$ and α-nitrosylHb Containing Erythrocytes α-nitrosylHb was prepared by an aerobic, stoichiometric combination of isolated nitrosylated α-subunits and isolated oxy β-subunits of human Hb. The resultant product, α(Fe—NO)$_2$β(Fe—O$_2$)$_2$ was used immediately or stored at liquid nitrogen temperature. Nitric oxide is so tightly bound to the α-subunits (an estimated $K_D$≈10$^{-15}$M) that neither detectable escape of NO from the α-subunits to media nor inter-subunit transfer of NO to the β-subunits has been observed during preparation, experiments, and storage, as long as the β-subunits are kept ligated. On the other hand, the NO bound to the β-subunits moves readily to the deoxy α-subunits. An isotonic suspension of washed erythrocytes was exposed to slow NO-generating systems under anaerobic conditions, while progress of α-heme nitrosylation of the intra-erythrocyte Hb was continually monitored by EPR. When slightly more than 50% of the total heme of the intra-erythrocyte Hb became nitrosylated, the NO-generating systems were removed by several cycles of repeated washing/low speed centrifugation. The washed erythrocyte suspension was anaerobically maintained at 0° C. until the transfer of NO from the β-subunits to the α-subunits has reached near completion. Then the erythrocyte suspension was exposed to $O_2$ and stored at 0° C. for an extended period.

EPR Measurements

EPR measurements were carried out with a Varian E106 X-band EPR spectrometer operated at 9.11 GHz with field modulation of 100 kHz, modulation amplitude of 2.0 gauss, and microwave power of 20 mW at liquid nitrogen temperature. Hemoglobin preparations, which were dissolved at 0.5 mM heme in appropriate buffers, were oxygenated by purging with pure $O_2$ gas or deoxygenated by repeated vacuum evacuation/purging with $O_2$-free argon gas at 15° C. for 30 min prior to freezing for EPR measurements.

Oxygen Equilibrium Measurements

Oxygen equilibrium measurements were carried out with a modified version of the Imai cell (Imai, K., *Allosteric Effects in Hemeoglobin*, Cambridge University Press, London (1982)) using either an Olis-Cary 118 dual-beam spectrophotometer (Bogart, Ga.) for solution or an Olis-Hitachi 557 dual-wavelength spectrophotometer (Bogart, Ga.) for erythrocyte suspension.

The above example establishes that methods and compositions of the present invention are suitable and useful for treating erythrocytes with NO to enhance oxygen delivery of Hb in erythrocyte containing solutions, such as whole blood and blood components or derivatives.

EXAMPLE 2

We have found that partially NO-bound hemoglobin (Hb) that is formed under physiological conditions is a new $O_2$ carrier which can deliver $O_2$ to tissues as effectively as normal Hb, in fact, even better than normal Hb under acidic conditions that are expected in tissues during high metabolic activities. This was demonstrated by preparing pure α-nitrosylHb and measuring its $O_2$ binding characteristics in solution. The molecular mechanism of NO-induced structural changes in Hb has been elucidated on the basis of the well-known coordination properties of NO and Hb and by comparison with structure and function of mutant $HbM_{Iwate}$ and $HbM_{Boston}$.

We conclude that Hb simultaneously acts as an efficient NO scavenger and an effective $O_2$ carrier and that NO in the blood not only acts as a vasodilator, as is well known, but also helps Hb to delivery $O_2$ more efficiently to peripheral tissues. Our finding explains why clinical "inhaled NO" treatment of newborns with persistent hypertension causes no acute adverse effect.

More importantly, our finding points to the practical possibility of rejuvenating the expired blood for transfusion. Huge amounts of blood at blood banks are discarded after certain periods of storage, because the concentration of 2,3-bisphosphoglycerate (BPG), a natural allosteric effecter, decreases and the intra-erythrocyte pH also decreases, rendering Hb to become a high-affinity state. Thus, the stored blood becomes ineffective for transfusion. As many compounds including BPG and other allosteric effecters are impermeable to the erythrocyte membrane, external administration of these compounds cannot restore their intra-erythrocyte concentration. On the other hand, NO is permeable to the erythrocyte membrane.

Furthermore, α-nitrosylHb has been demonstrated to have a low $O_2$-affinity, having a right-shifted $O_2$-binding curve, analogous to Hb in the presence of BPG. Therefore, we proposed the idea of converting the normal Hb in the stored blood to α-nitrosylHb to improve its efficiency of $O_2$ delivery of the expired blood.

The above example establishes that methods and compositions of the present invention are suitable and useful for treating erythrocytes with NO to enhance oxygen delivery of Hb in erythrocyte containing solutions, such as whole blood and blood components or derivatives.

EXAMPLE 3

Nitric oxide (NO) acts as a regulator of a number of vital cellular, physiological and biochemical reactions, principally by activating soluble guanylate cyclases in production of cGMP, a second messenger in signal transduction in various tissues. Nitric oxide in the blood is well maintained at a steady-state level of the order of micromolar by the dynamic balance between the continuous supply of NO by endothelial NO syntheses and other sources and the rapid scavenging of NO by oxy hemoglobin (oxyHb) in the erythrocytes. Nitric oxide in the blood rapidly diffuses into erythrocytes and reacts with oxyHb to form metHb and $NO_2^-/NO_3^-$. MetHb so formed is immediately reduced to deoxyHb by active metHb reductase in the erythrocytes. The relative concentration of NO (<1 μM in plasma) with respect to that of Hb (20 mM heme in the erythrocytes) is very limited in the blood. Under such conditions, NO converts deoxyHb preferentially to α-nitrosylHb [α(Fe—NO)α(Fe)β(Fe)$_2$ or α(Fe—NO)$_2$β(Fe)$_2$]. We found it to be an allosteric, low-affinity $O_2$-carrier ($P_{50}$=30 and 70 torr for Hb and α(Fe—NO)$_2$β(Fe)$_2$, respectively) under physiological conditions to facilitate more efficient delivery of $O_2$ to peripheral tissues. EPR and NMR measurements indicate that the Fe-His(F8) bonds in the α-subunits of deoxy α-nitrosylHb [α(Fe—NO)$_2$β(Fe)$_2$] are broken, causing its quaternary structural transition to T-(low-affinity extreme) states having an extremely low $O_2$-affinity, as observed in other known T-(low-affinity extreme) Hbs such as $HbM_{Iwaste}$ [α(Fe[III]$^{87}$His→Tyr)$_2$β(Fe)$_2$], $HbM_{Boston}$[α(Fe[III]$^{58}$His→Tyr)$_2$β(Fe)$_2$ and α(protoporphyrin)$_2$β(Fe)$_2$] (Fujii, et al., *J. Biol. Chem.* 268:15386–15393 (1955)). α(Fe—NO)$_2$β(Fe)$_2$, which is in a predominantly T-(low-affinity extreme) state, reversibly forms the α Fe-His(F8) bonds upon oxygenation of the β-subunits and shifts its quaternary structure toward R-states, so that α(Fe—NO)$_2$β(Fe)$_2$ becomes an allosterically-sensitive, low-affinity $O_2$-carrier, which becomes the deoxy state at the venous $P_{O2}$=40 torr by releasing almost all the bound $O_2$, where normal Hb remains 75%-oxygenated. Thus, the NO in the blood facilitates increased oxygen delivery to tissues through the vasodilation as well as the formation of an allosteric, low-affinity Hb, α(Fe—NO)$_2$β(Fe)$_2$. Binding of NO to Hb as well as soluble guanylate cyclase causes the trans-axial breakage of the Fe-His bond in their heme prosthetic groups, resulted in alteration of their protein conformation (to the T-(low-affinity extreme) low-affinity state in Hb and to the activated state in soluble guanylate cyclase). Thus, the unique feature of NO as the physiological regulator relies solely on its unique coordination property to transaxially break the heme Fe-His bond upon ligation, due to its preference to a 5-coordinated heme structure over a 6-coordinate state.

The above example establishes that methods and compositions of the present invention are suitable and useful for treating erythrocytes with NO to enhance oxygen delivery of Hb in erythrocyte containing solutions, such as whole blood and blood components or derivatives.

EXAMPLE 4

The following method provides treated whole blood having most or all of the Hb present as at least about 80–99 percent α-nitrosyl-Hb. The erythrocyte containing diluent is provided in a physiologically compatible buffer and the treatment method comprises (a) deoxygenating the Hb in the erythrocytes; and
(b) providing NO in the diluent in 50–55% equivalent amounts of the heme concentration of the Hb, such that at least about 80–99 percent of the Hb is converted to α-nitrosyl-Hb.

Heparinated blood (10 ml), which is obtained from the Red Cross Blood Bank, is suspended in a 2-fold volume of chilled isotonic sucrose solution (the isotonic sucrose solution consists of 250 mM sucrose, 5 mM KCl, 2 mM $NaH_2PO4$, 1 mM $MgCl_2 6H_2O$, and 10 mM glucose.), centrifuged at 1,500 g for 10 minutes at 4 degrees C. After carefully decanting the supernatant and the buffy layer of leukocytes, the loosely packed precipitate of erythrocytes is re-suspended in a fresh isotonic sucrose solution. The centrifugal washing procedure is repeated two more times.

The final concentration of hemoglobin in the loosely packed, washed erythrocytes is approximately 20 mM heme (or ca. 5 mM tetrameric hemoglobin). The loosely packed precipitate of washed erythrocytes is re-suspended in a 2-volume of chilled 0.15M sodium-potassium phosphate buffer, pH 5.8 (The phosphate buffer is prepared by mixing 0.15M $Na_2HPO_4$ and 0.15 M $KH_2PO_4$ to adjust the pH to 5.8.), transferred into a 300 ml-Kieldahl type flask with a rubber stopper, to which two stainless-steel gauge 20 needles with three-way stopcocks are inserted in. These needles serve as the inlet and outlet of purging gases. By flowing pure argon or nitrogen (grade 5) into the flask, which is continually shaken gently at 4 degrees C., the erythrocyte suspension is deoxygenated. Observing the change in the color of the erythrocyte suspension readily follows the progress of deoxygenation.

After prolonged deoxygenation, the color changes from bright red (of oxy hemoglobin) to deep purple (of deoxy hemoglobin). Then, a 10-fold excess (to heme) quantity of a 50 mg/ml solution of sodium dithionite ($Na_2S_2O_4$) (the sodium dithionite solution is prepared by dissolving 50 mg/ml of sodium dithionite into deoxygenated distilled water. The presence of oxygen in distilled water causes formation of hydrogen peroxide, which interferes with the preparative procedure) is added into the suspension. Then closing the stopcock terminates the gas flow.

The erythrocyte suspension is gently stirred for one minute and let stand on ice for 10 minutes. A 52–55% equivalent (to heme) quantity of a freshly prepared 50 mg/ml solution of sodium nitrite ($NaNO_2$) is injected into the suspension through the needle. Sodium nitrite reacts stoichiometrically and immediately with sodium dithionite and forms nitric oxide that combines with the $\alpha$-heme groups of hemoglobin.

The slightly acidic (pH5.8) sucrose buffer of the suspension promotes the formation of $\alpha$-nitrosyl hemoglobin. A ca. 2–5% excess of nitrite added is to ensure the ligation of NO to all the $\alpha$-subunits of hemoglobin and thus reducing the possibility of unreacted hemoglobin molecules remaining. The addition of a large excess of sodium nitrite into the suspension must be avoided because the ligation of NO to the $\beta$-subunits occurs at larger quantities of nitrite.

After allowing the suspension stand for one hour at 4 degrees C., the rubber stopper of the flask is removed. The suspension is then rapidly washed three times with chilled, deoxygenated isotonic sucrose solution to remove excess reagents and reaction byproducts. Then, the suspension is exposed to air to produce oxygenated ($\alpha$-nitrosyl hemoglobin or $\alpha$-nitrosyl, $\beta$-oxy hemoglobin ($\alpha$(Fe—NO)$_2$$\beta$(Fe—$O_2$)$_2$). The product is best identified by electron paramagnetic resonance spectroscopy, as described in Example 1 above. The so-prepared suspension of erythrocytes containing $\alpha$-nitrosyl hemoglobin is stored on ice for an extended period.

The above example establishes that methods and compositions of the present invention are suitable and useful for treating erythrocytes with NO to enhance oxygen delivery of Hb in erythrocyte containing solutions, such as whole blood and blood components or derivatives. Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as can be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional method steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Beckman, J. S., et al., *Proc. Natl. Acad. Sci. USA* 87:1620–1624 (1990)
Doyle, M. P., and Hoekstra, J. W., *J. Inorg. Chem.* 14:351–358 (1981)
Erikson, L. E. G., *Biochem. Biophys. Res. Cornmun,* 203:176–181 (1994)
Fujii, M., et al., *J. Biol. Chem.* 268:15386–15393 (1993)
Gibson, Q. H., and Roughton, F. J. W., *Proc. Roy. Soc. London B. Biol. Sci.* 163:197–205 (1965)
Hayashi, A., et al., *J. Biol. Chem.* 241:79–84 (1966)
Henry, Y. and Banerjee, R., *J. Mol. Biol.* 73:469–482 (1973)
Hille, R., et al., *J. Blot Chern* 254:12110–12120 (1979)
Hori, H., Okazaki, *Hemoglobin Conference* (1995)
Huang, T.-H., *J. Biol. Chem.* 254:11467–11474 (1979)
Ignarro, L. E., et al., *Proc. Natl. Acad. Sci. USA* 84:9265–1969 (1987)
Imai, K., *Allosteric Affects in Hemeoglobin*, Cambridge University Press, London (1982)
Jia, L., et al., *Nature* 380:221–226 (1996)
Kosaka, H., et al., *Am. J. Physiol.* 266:C1400–C1405 (1994)

Kosaka, H., and Seiyama, A., *Nature Medicine* 3:456–459 (1997)

Kosaka, H., et al., *Am. J. Physiol.* 266:C1400–C1405 (1994))

Kosaka, H. and Seiyama. A., *Biochem. Biophys. Res. Commun.* 218:749–752 (1996)

Maxwell, J. C., and Caughey, W. S., *Biochemistry* 15:388–396 (1976)

Moore, E. G., and Gibson, Q. H., *J. Biol. Chem.* 251:2788–2794 (1976)

Nagai, K., and Kitagawa, T., *Proc. Natl. Acad Sci. USA* 77:2033–2037 (1980)

Nagai, K., et al., *Biochem. Biophys. Acta* 532:17–28 (1978)

Nathan, C., *FASEB J.* 6:3051–3064 (1992)

Palmer, R. M. J., et al., *Nature* 327:524–526 (1987)

Pepke-Zaba, J., et al., *Lancet* 338:1173–1174 (1991)

Perutz, M. F., *Nature* 228:726–739 (1970)

Rein, H., et al., *FEBS Lett* 93:24–26 (1972)

Shiga, T., et al., *Biochemistry* 8:378–383 (1969)

Stamler, J. S., et al., *Science* 258:1898–1900 (1992)

Suzuki, T., et al., *Biochem. Biophys. Res. Commun.* 19:691–695 (1965)

Szabo, A., and Perutz, M. F., *Biochemistry* 15:4427–4428 (1976)

The U.S. Environmental Protection Agency, *Publication* AP-84 (1971)

Traylor, T. G., and Sharma, V. S., *Biochemistry* 31:2847–2849 (1992)

Wayland, B. B., and Olson, L. W., *J. Am. Chem. Soc.* 96:6037–6041 (1974)

Wink, D. A., et al., *Science* 254:1001–1003 (1993)

Yonetani, T., et al., *J. Biol. Chem.* 247:2447–2455 (1972)

Yonetani, T., *Proc. Japanese Medical Soc. Magn. Resom*, Kanagawa, Japan (1995)

Yonetani, T., and Tsuneshige, A., *Biophys. J.* 70:A220 (1996)

Yonetani T., (Abstract 106S), *Proc. 35th ESR Discussion Conference*, Yamagata, Japan (1996) p. 15

What is claimed is:

1. A method for treating erythrocytes that contain hemoglobin comprising, in the order mentioned:

i) deoxygenating the erythrocytes under anaerobic conditions to produce erythrocytes that contain deoxyhemoglobin;

ii) providing nitric oxide to the erythrocytes to convert the $\alpha$ subunits of the deoxyhemoglobin to $\alpha$-Fe-nitrosyl hemoglobin whereby at least 80% of the $\alpha$-hemoglobin subunits are $\alpha$-Fe-nitrosyl hemoglobin and essentially no $\beta$-hemoglobin subunits are nitrosated; and iii) oxygenating the erythrocytes, thereby obtaining erythrocytes comprising oxygenated $\alpha$-nitrosyl hemoglobin, $\alpha(Fe\text{—}NO)_2\ \beta(Fe\text{—}O_2)_2$.

2. The method according to claim 1, wherein no $\beta$-hemoglobin subunits are nitrosated in said step ii).

3. The method according to claim 1, wherein the amount of nitric oxide provided to the erythrocytes is not more than 10% excess of the stoichiometric amount of $\alpha$-hemoglobin subunits.

4. The method according to claim 1, wherein said anaerobic conditions are attained by treating said erythrocytes under an inert gas atmosphere and then treating the erythrocytes with a reducing agent.

5. The method according to claim 4, wherein said reducing agent is a dithionite.

6. The method according to claim 1, wherein said nitric oxide is added by producing said nitric oxide as the product of a chemical reaction in a diluent containing said erythrocytes.

7. The method according to any one of claims 1–6, wherein said erythrocytes to be treated are contained in whole blood or in a diluent which comprises at least one blood component.

8. The method according to claim 7, wherein said whole blood or said diluent comprising said erythrocytes has been stored for at least 3 weeks before being treated.

9. A method for producing an oxygen delivering composition for transfusion into a mammal comprising, in the order:

i) deoxygenating erythrocytes under anaerobic conditions to produce erythrocytes that contain deoxyhemoglobin;

ii) providing nitric oxide to the erythrocytes to convert the $\alpha$ subunits of deoxyhemoglobin to $\alpha$-Fe-nitrosyl hemoglobin, whereby at least 80% of the $\alpha$-hemoglobin subunits are $\alpha$(Fe-nitrosyl) hemoglobin and essentially no $\beta$-hemoglobin subunits are nitrosated; and iii) oxygenating the erythrocytes, thereby obtaining an oxygen delivering composition comprising oxygenated $\alpha$-nitrosyl hemoglobin, $\alpha(Fe\text{—}NO)_2\beta(Fe\text{—}O_2)_2$ suitable for transfusion into a mammal.

10. The method according to claim 9, wherein no $\beta$-hemoglobin subunits are nitrosated in step ii).

11. The method according to claim 9, wherein the amount of provided to the erythrocytes is not more than 10% excess of the stoichiometric amount of $\alpha$ hemoglobin subunits.

12. The method according to claim 9, wherein said anaerobic conditions are attained by treating said erythrocytes under an inert gas atmosphere and then treating the erythrocytes with a reducing agent.

13. The method according to claim 12, wherein said reducing agent is a dithionite.

14. The method according to claim 9, wherein said nitric oxide is added by producing said nitric oxide as the product of a chemical reaction in a diluent comprising said erythrocytes.

15. The method according to any one of claims 9–14 wherein said erythrocytes to be subjected to step i) are contained in whole blood or in a diluent comprising at least one blood component.

16. The method according to claim 15, wherein said whole blood or said diluent has been stored for at least 3 weeks before said erythrocytes are subjected to said step i).

* * * * *